(12) United States Patent
Kauppinen

(10) Patent No.: US 7,208,737 B2
(45) Date of Patent: Apr. 24, 2007

(54) PHOTOACOUSTIC DETECTOR

(75) Inventor: Jyrki Kauppinen, Ilmarinen (FI)

(73) Assignee: Noveltech Solutions, Ltd., Turku (FI)

( * ) Notice: Subject to any disclaimer, the term of this patent is extended or adjusted under 35 U.S.C. 154(b) by 25 days.

(21) Appl. No.: 10/529,777

(22) PCT Filed: Sep. 19, 2003

(86) PCT No.: PCT/FI03/00683

§ 371 (c)(1),
(2), (4) Date: Sep. 23, 2005

(87) PCT Pub. No.: WO2004/029593

PCT Pub. Date: Apr. 8, 2004

(65) Prior Publication Data

US 2006/0138327 A1    Jun. 29, 2006

(30) Foreign Application Priority Data

Sep. 30, 2002  (FI) ............................ 20021734

(51) Int. Cl.
*G01J 5/02* (2006.01)
(52) U.S. Cl. ............................................. 250/339.13
(58) Field of Classification Search ............ 250/339.13
See application file for complete search history.

(56) References Cited

U.S. PATENT DOCUMENTS 4,507,170 A    3/1985  Myhre (Continued)

FOREIGN PATENT DOCUMENTS

| EP | 1 211 501 A1 | 6/2002 |
|---|---|---|
| EP | 1 239 698 A1 | 9/2002 |
| WO | 03/046498 A1 | 6/2003 |

OTHER PUBLICATIONS

De Paula, M H et al., "High-Sensitivity optical microphone for photoacous tics", Rev. Sci. Instrum. 63(6), Jun. 1992, 1992 American Institute of Physics.
De Paula, M H et al., "Optical microphone for photoacoustic spectroscopy", J.Appl.Phys. 64(7), Oct. 1, 1988, 1988 American Institute of Physics.

(Continued)

*Primary Examiner*—Constantine Hannaher
*Assistant Examiner*—Marcus Taningco
(74) *Attorney, Agent, or Firm*—Buchanan, Ingersoll & Rooney PC

(57) ABSTRACT

The invention relates to a photoacoustic detector, comprising at least a first chamber ($V_0$) suppliable with a gas to be analyzed, a window for letting modulated and/or pulsed infrared radiation and/or light in the first chamber ($V_0$), a second chamber (V), which constitutes a measuring space with a volume V and which is in communication with the first chamber by way of an aperture provided in a wall of the first chamber, at least one sensor, which is arranged in the wall aperture of the first chamber and arranged to be movable in response to pressure variations produced in the first chamber by absorbed infrared radiation and/or light, and means for measuring the sensor movement. The means for measuring the sensor movement include at least one or more light sources for illuminating the sensor or a part thereof and one or more multi-detector detectors for the reception of light reflected from the sensor and for measuring the sensor movement as optical angular and/or translatory measurement. The invention relates additionally to a measuring system in a photoacoustic detector, a method for measuring the movement of a sensor in a photoacoustic detector, and a method in the optimization of a photoacoustic detector.

20 Claims, 6 Drawing Sheets

U.S. PATENT DOCUMENTS

Figure 1:
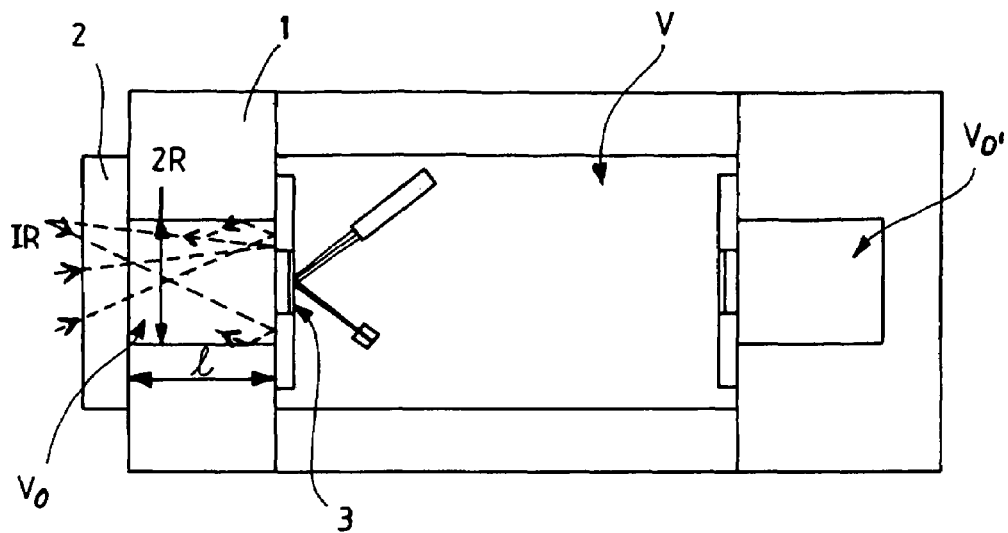

| | | |
|---|---|---|
| 5,822,061 A | 10/1998 | Delhaye et al. |
| 6,210,331 B1 | 4/2001 | Raz |
| 6,222,190 B1 | 4/2001 | Bernstein et al. |
| 6,474,168 B1 | 11/2002 | Meringdal |
| 2003/0002129 A1 | 1/2003 | Kobayashi et al. |
| 2003/0173507 A1 | 9/2003 | Paritsky et al. |

OTHER PUBLICATIONS

Nicolas Ledermann et al., "Piezoelectric Cantilever Microphone for Photoacoustic GAS Detector", Integrated Ferroelectrics, 2001, vol. 35, pp. 177-184.

PHOTOACOUSTIC DETECTOR

The invention relates to a photoacoustic detector as set forth in the preambles of the appended independent claims, and to a measuring system in a photoacoustic detector, as well as to a method for measuring the movement of a sensor in a photoacoustic detector.

When infrared radiation or light in general falls on a gas-filled chamber containing a gas to be analyzed at a partial pressure $p_x$ and a carrier gas at a partial pressure $p_N$ (often typically nitrogen), radiation will be absorbed by the gas $p_x$. After the absorption process, energy converts to thermal movement at a certain time constant $\tau$ (e.g. $10^{-5}$s). Thus, temperature of the total gas increases by $\Delta T$ per unit time. The increase of temperature results also in a pressure increase $\Delta p$.

A typical photoacoustic detector comprises a chamber, which is suppliable with a gas to be analyzed, a window for letting modulated or pulsed infrared radiation or light in the chamber, and a pressure sensor adapted to measure pressure variations produced by absorbed infrared radiation or light in the chamber. The pressure sensor comprises typically a microphone, a thin Mylar or metal film. A photoacoustic detector can be used for measuring or detecting infrared radiation in general, but one specific and important application of a detector deals with the measurement and detection of gases or gas mixtures regarding for example air quality and pollution.

In microphones, the movement of a film (Mylar) is usually measured capacitively. The Mylar film is coated with metal and placed in the proximity of another solid metal diaphragm. The result is a capacitor, having a capacitance $$C = \frac{\varepsilon_r \varepsilon_0 A}{h}, \tag{a}$$

where h represents a distance between the films at rest, A is a surface area of the films, $\varepsilon_r \varepsilon_0$ is a dielectric constant for a gas present between the sheets and $\varepsilon_0$ the same for a vacuum. The measurement of C provides h which gives the movement of a Mylar film, because $$\Delta C = -\frac{\varepsilon_r \varepsilon_0 A}{3h^2} \Delta h, \tag{b}$$

where $\Delta h$ is a change of distance in the middle and $\Delta h/3$ is an average change of distance. Further $$\frac{\Delta C}{C} = -\frac{\Delta h}{h} \tag{c}$$

or $$|\Delta h_{min}| \approx \frac{h}{C/\Delta C} = \frac{h}{S/N}, \tag{d}$$

where S/N is a signal-to-noise ratio in measuring electronics.

Capacity measurements of the prior art are limited by a gas flow present between the sheets, as h changes. As the gap h decreases, the gas is forced to flow out from between the sheets and return when h is increasing. The flow has inertia and that requires energy. A result of this is that, the higher the angular oscillation frequency ω of a diaphragm and the smaller h, the more the flow decreases the amplitude of a diaphragm movement. Thus, h cannot be decreased infinitely, as this would augment a signal $\Delta C$. Therefore, the commercially available microphones function at the limits of physical laws and their responsivity cannot be improved in that regard.

In their publication [1], Nicolas Lederman et al. disclose a photoacoustic detector for a sensor, wherein the sensor is fabricated from a cantilever type film, which responses to the movement of a gas in the chamber of a photoacoustic detector and in which film is integrated a piezoelectric element registering the cantilever movement. A problem with the sensor set forth in the publication is that the cantilever's resonance frequency has been omitted. It is likely that a piezoelectric element attached to a sensor increases the sensor's resonance frequency and thus deteriorates the sensor's response. The sensor presented in the publication is quite inaccurate and, therefore, not suitable for high precision applications. Neither does the publication say anything about optimization of a chamber and a sensor in the photoacoustic detector, i.e. the ratio of the size of a chamber to that of a sensor.

In their publications [2] and [3], M. H. de Paula et al. also disclose an alternative to a traditional diaphragm solution. The publications propose that a pellicle be fitted over a small duct in a photoacoustic detector cell at a distance of about 0,1 mm from the duct. According to what is stated in the publication, the pellicle is not provided with a so-called rim around itself, the pellicle thus extending beyond the duct boundaries, i.e. the question is not about a cantilever like the one shown in publication [1]. Hence, the fundamental problem in the publications of de Paula et al. is indeed the fact that the pressure to be measured and existing in a photoacoustic detector cell is only applied to a small portion of the total area of the pellicle, resulting in a considerably lower response. In addition, there is a leak from under the pellicle which is large with respect to the duct size, which further reduces the pellicle response. The publications [2] and [3] further describe an optical angular measurement for measuring the movement of a pellicle. However, the shape of a pellicle set forth in the cited publications is in practice unfavourable for angular measuring. Consequently, the solution proposed in publications [2] and [3] is not sufficiently responsive for highly accurate measurements and high precision applications.

Another problem in photoacoustic detection is a disturbance thereof as a result of external sounds. Thus, if the intra-chamber sound, infiltrated from outside the measuring instrument, is more powerful than the intrinsic noise of a system, the improvement regarding the sensitivity (response) of a detector system does not improve the determination of a gas to be analyzed. A typical method for reducing disturbances created by external sounds is sound proofing. Proofing is capable of damping external sounds at a coefficient of 10000–100000.

Another prior known means of reducing disturbances caused by external sounds comprises the use of double detection for a partial reduction of interfering sounds. In prior known double detection systems, a measuring system is provided which is identical to the regular measuring system, said identical system being denied the access of light, and it only measures sound within the chamber. Then, according to the solutions of prior art systems, there is performed a direct amplification of the difference between the actual measuring signal and a reference signal given by the identical measuring system. However, a problem with double detection systems as described above is e.g. that these systems only function in a special situation over a narrow frequency band. The problem is due to a phase difference created between sensors in the measuring systems.

Consequently, it is an object of the photoacoustic detector and the measuring system in the photoacoustic detector as well as the method for measuring the movement of the sensor in the photoacoustic detector, in accordance with the invention, to eliminate or at least alleviate the above-described prior art problems.

Another object of the photoacoustic detector and the measuring system in the photoacoustic detector as well as the method for measuring the movement of the sensor in the photoacoustic detector, in accordance with the invention, is to provide an accurate and highly sensitive photoacoustic detector.

A further object of the present invention is to provide a photoacoustic detector and a measuring system in a photoacoustic detector, wherein the effect of disturbance factors resulting from external sounds on a measuring result has been reduced.

In order to fulfill the above objects, among other things, the photoacoustic detector and the measuring system in the photoacoustic detector as well as the method for measuring the movement of the sensor in the phoacoustic detector, all according to the invention, are principally characterized by what is set forth in the characterizing clauses of the independent claims.

Thus, in a typical photoacoustic detector of the present invention, the means for measuring the sensor movement include at least one or more light sources for illuminating the sensor or a part thereof and one or more multi-detector detectors for the reception of light reflected from the sensor of the detector and for measuring the sensor movement as optical angular and/or translatory measurement. In this context, the term multi-detector detector is used in reference to a detector, which comprises two, three or more detectors, i.e. which can be referred to as double detector, triple detectors etc., respectively. In other words, these are detectors, from which a number of separate measuring signals can be obtained, i.e. two measuring signals from a double detector and three measuring signals from a triple detector, etc. Multi-detector detectors can be configured by linking together a number of individual detectors or, for example, by fabricating three detectors for a single frame. For example, an array detector, such as a CCD array detector, can also be used as a multi-detector detector as discussed in the present context. A CCD array detector can be used for replacing both a double detector and a triple detector.

The result of this is a measuring method and system which is virtually almost non-interfering with the function of a sensor. Non-interference with measuring refers to the condition that the measuring method does not in practice disturb and/or suppress the movement of a sensor, i.e. the effect of optical particles on the movement of a door in practical measuring applications must be considered in this sense insignificant. Preferably, the light source to be used is a laser or a thin filament. A filament offers the advantage of providing a broad range of linearity.

The advantage of a double detector is that the measurement of a sensor movement can be implemented by using both angular measurement and translatory measurement. In angular measurement, it is preferred that the focus of a light beam emitted by a light source be applied approximately on the surface of a double detector. In translatory measurement, it is typically preferred that the focus of a light beam emitted by a light source be applied approximately on the surface of a door or a diaphragm, as well as on a double detector.

In one preferred photoacoustic detector of the invention, the means for measuring the sensor movement include at least a laser functioning as a light source, at least one optical lens for focusing the laser beam, a reference mirror, a beam splitter for splitting the laser beam for the sensor and the reference mirror, and a triple or array detector, functioning as the detector, for receiving the laser beams coming from the beam splitter. In a highly preferred form, the reference mirror is arranged in such a way that the triple or array detector develops ¾ of the interference fringe.

In a highly preferred photoacoustic detector of the present invention, the means for measuring the sensor movement further include a fixed plane mirror and a fixed end mirror, which are arranged in such a manner that the laser light travels to the end mirror and back, reflecting reciprocally between the sensor and the plane mirror. In a very preferred form, the plane mirror and/or the end mirror are arranged in such a way that the laser beam, adapted to travel from the beam splitter by way of the sensor to the end mirror, returns over the same optical path from the end mirror back to the beam splitter.

One highly preferred photoacoustic detector of the present invention comprises additionally a third chamber, which is closed and identical to the first chamber in terms of size and has an aperture which is identical to that included in the first chamber and connects the third chamber with the second chamber, and the aperture of the third chamber being closed with a sensor similar to that closing the aperture of the first chamber, and the movement of the sensor being measured in a manner similar to that used for measuring the movement of a sensor closing the first chamber aperture, as well as means for calculating the amplitudes of an actual measuring signal measured from the sensor fitted in the first chamber aperture and a reference signal measured from the sensor fitted in the third chamber aperture, and for working out a difference therebetween.

A typical measuring system of the present invention in a photoacoustic detector for measuring the movement of a sensor in a photoacoustic detector comprises at least a laser or a filament functioning as a light source, at least one optical lens for focusing a light beam, a reference mirror, a beam splitter for splitting the light beam for the sensor and the reference mirror, a fixed plane mirror and a fixed end mirror, which are arranged in such a manner that the light beam travels to the end mirror and back, reflecting reciprocally between the sensor and the plane mirror, and a triple or array detector, functioning as the detector, for receiving the light beams coming from the beam splitter.

In a typical method of the present invention for measuring the movement of a sensor in a photoacoustic detector, the measurement is implemented as an optical measurement, the sensor or a part thereof being illuminated and light reflected from the sensor being measured by means of a multi-detector detector. Thus, the sensor movement is measured as angular measurement by concentrating the focus of a light beam approximately on a double or array detector and by measuring the displacement of a reflected light beam by means of a double or array detector, or the sensor movement is measured as translatory measurement by concentrating the focus of a light beam approximately on the sensor surface and on a double or array detector and by measuring the displacement of a reflected light beam by means of a double or array detector, or the sensor movement is measured as translatory measurement by using an interferometer and by measuring the displacement of the interference fringe of a light beam reflected from the sensor by means of a triple or array detector. In this context, the reference to concentrating a light beam approximately on the surface of a sensor and/or on the surface of a double or array detector means that the focus of a light beam lies on the surface of a sensor and/or a double or array detector at such an accuracy which is technically possible.

Figure 8:
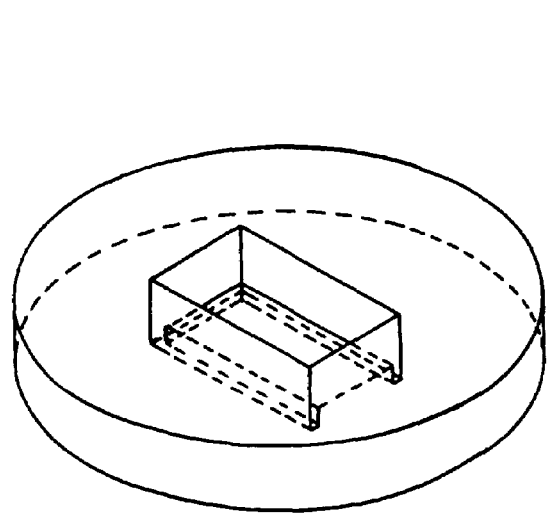
Figure 9A:
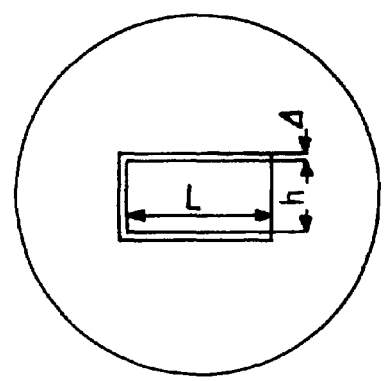
Figure 9B:
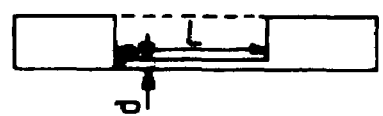
Figure 2:
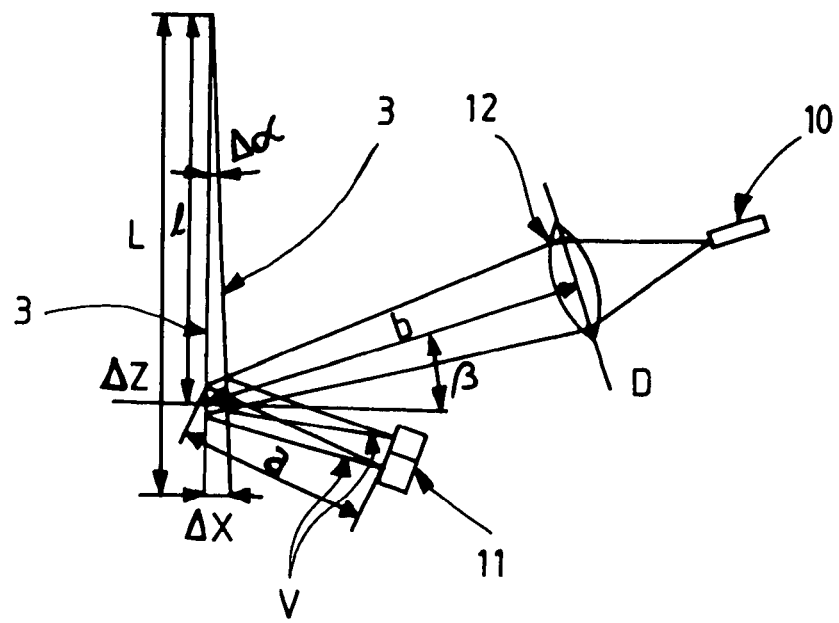
Figure 3:
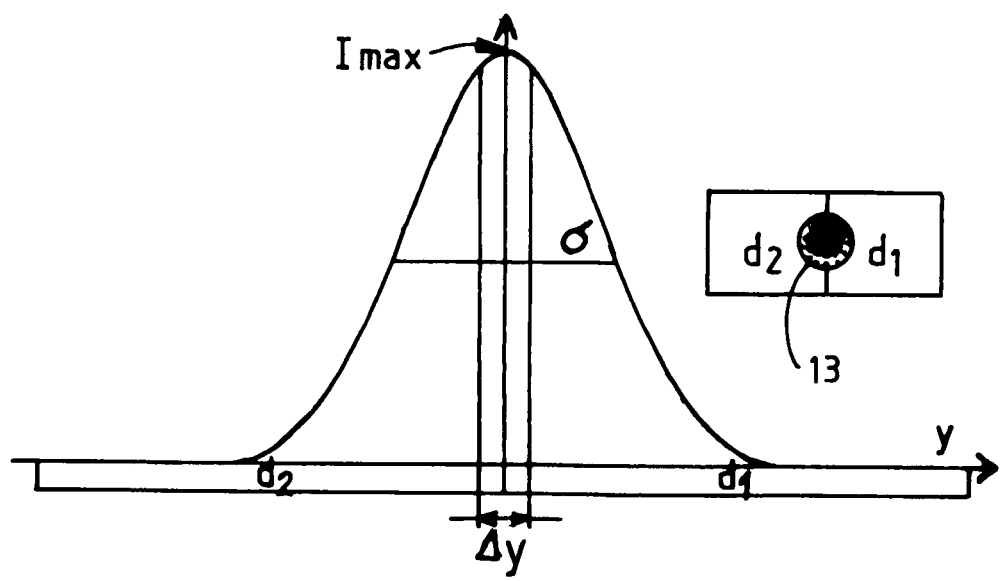
Figure 4:
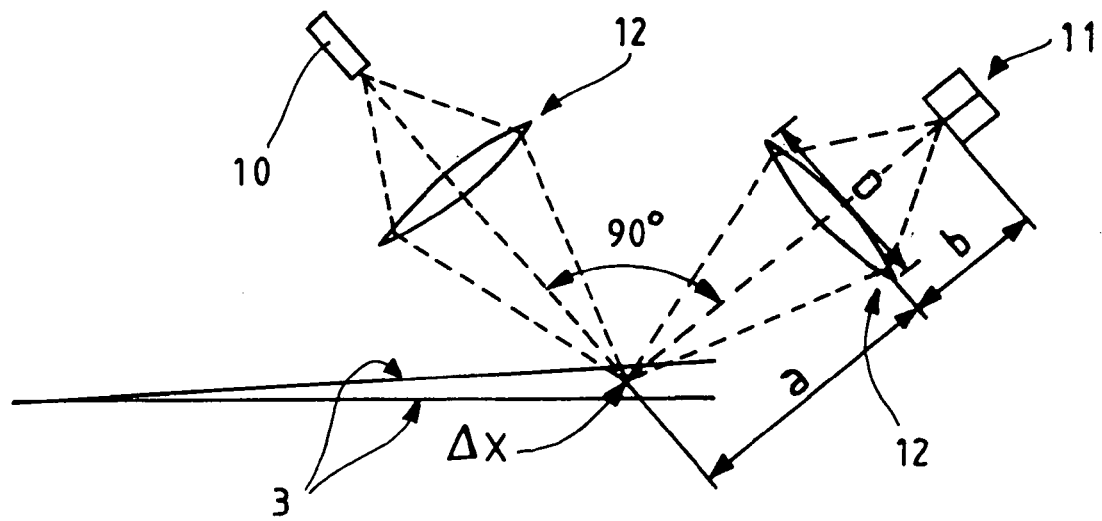
Figure 5:
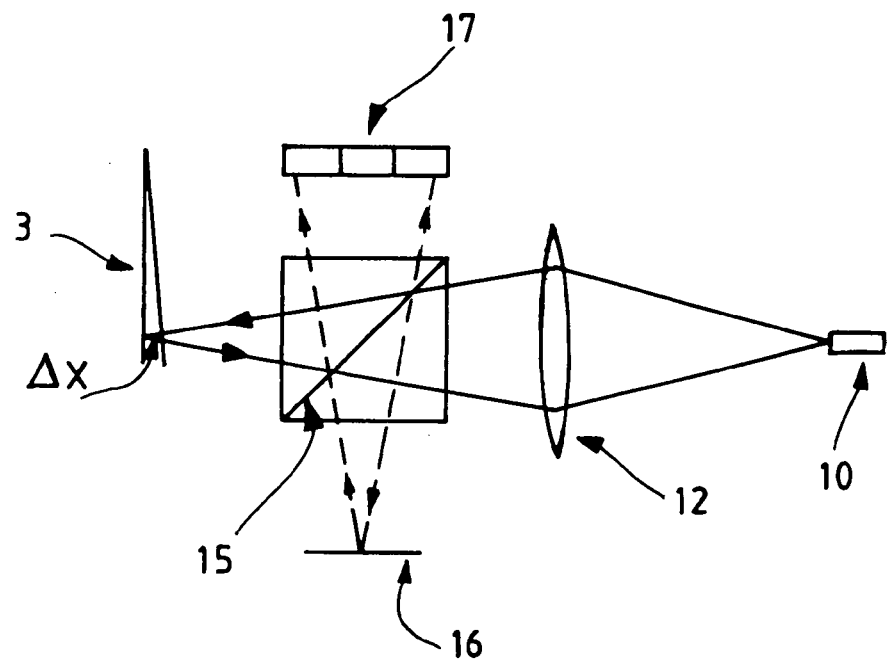
Figure 6:
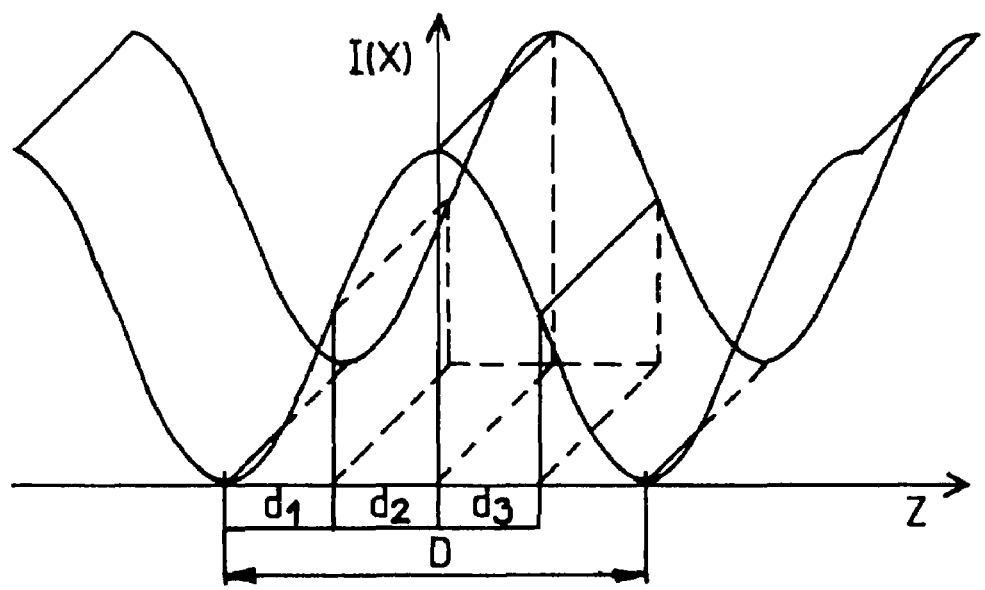
Figure 7:
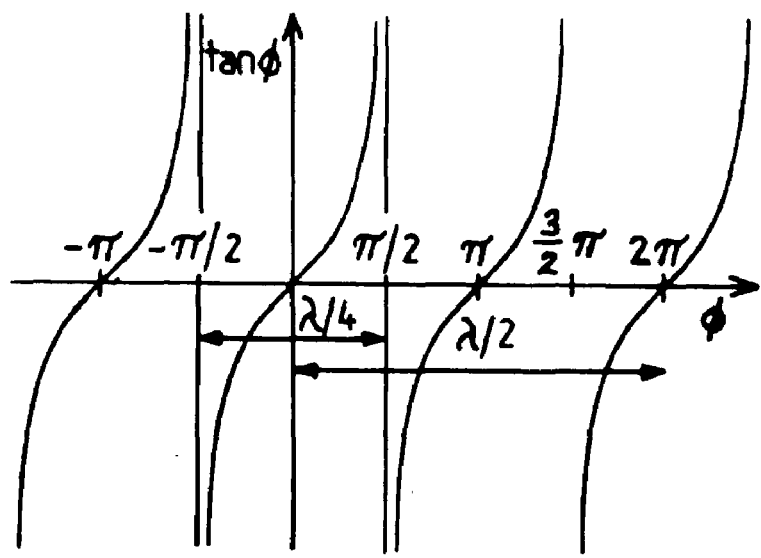
Figure 10A:
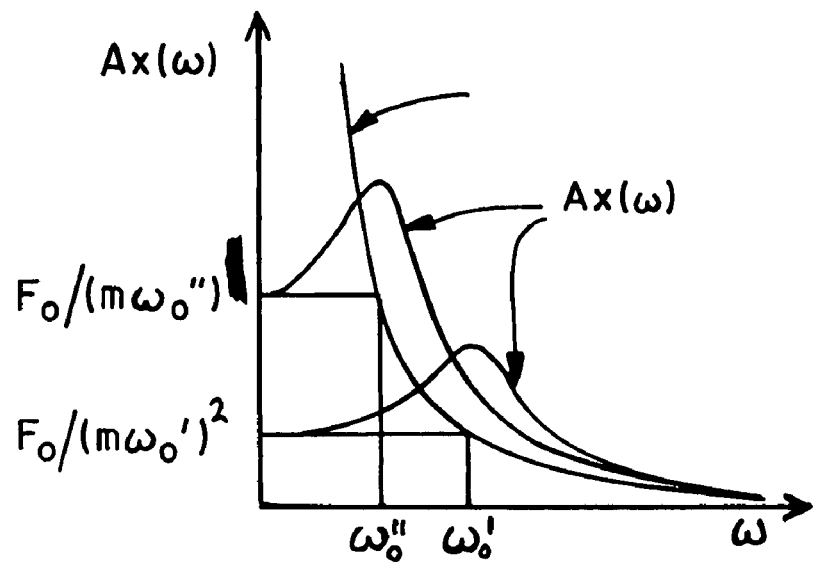
Figure 10B:
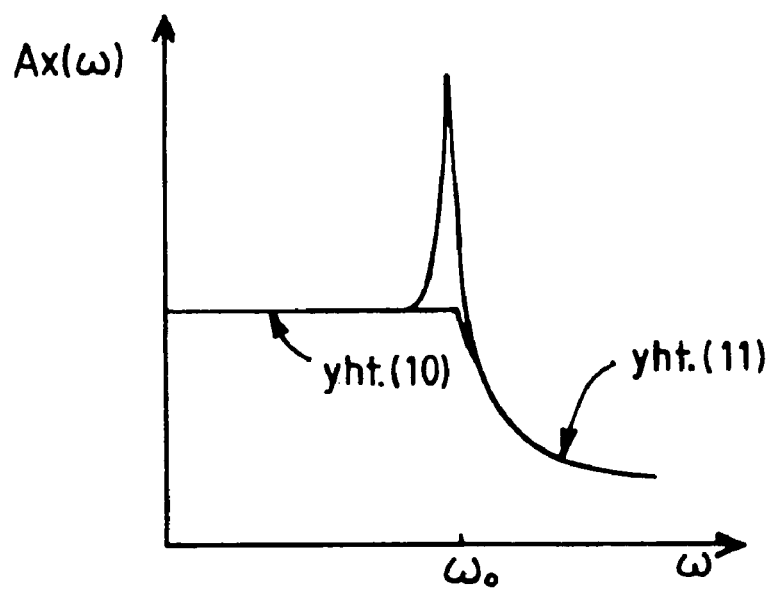
Figure 11:
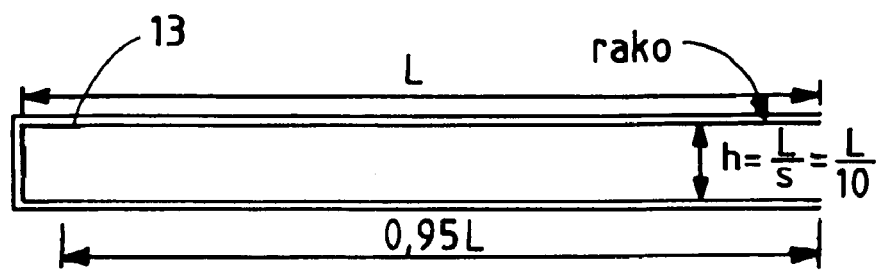
Figures 12A, 12B:
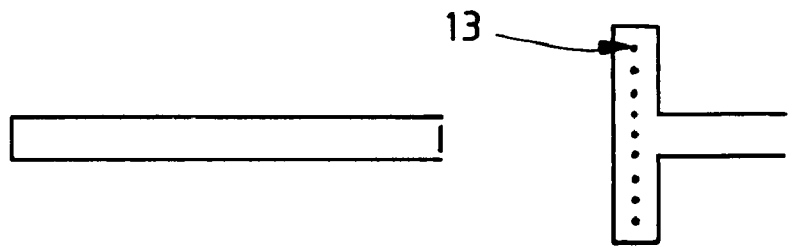
Figure 13:
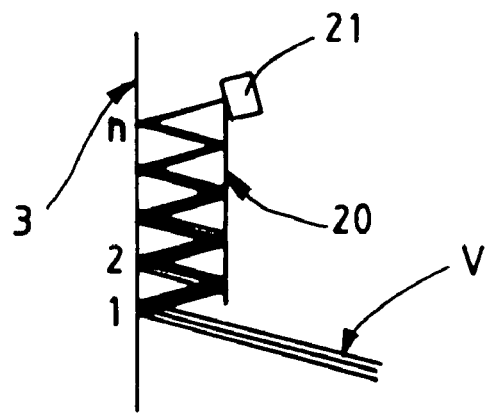

The invention will now be described in more detail with reference to the accompanying drawing, in which FIG. 1 shows schematically a design for a photoacoustic detector of the invention, FIG. 2 shows schematically a measuring system of the present invention for the movement of a pressure sensor door on the basis of angular variation of the door, FIG. 3 shows schematically a light intensity for a double detector in the measuring system of FIG. 2, FIG. 4 shows schematically a measuring system of the present invention for the movement of a pressure sensor door on the basis of a translatory measurement of the door, FIG. 5 shows schematically a measuring system of the present invention for the movement of a pressure sensor door, based on the use of a Michelson interferometer, FIG. 6 shows schematically an interference fringe developed on a triple detector in the measuring system of FIG. 5, FIG. 7 shows schematically discontinuities in a tangent, FIG. 8 shows schematically a pressure sensor for a photoacoustic detector of the invention obliquely from above, FIG. 9a shows schematically a pressure sensor for a photoacoustic detector of the invention from the front, FIG. 9b shows schematically a pressure sensor for a photoacoustic detector of the invention in a cross-section, FIG. 10a shows schematically the effect of a resonance angular frequency $\omega_0$ on an amplitude $A_x(\omega)$, FIG. 10b shows schematically modelling of a door resonance, FIG. 11 shows schematically one preferred door design for a photoacoustic detector of the present invention, FIGS. 12a and 12b show schematically a few optional door designs for a photoacoustic detector of the present invention, and FIG. 13 shows schematically a measuring system of the present invention for the movement of a pressure sensor door, by means of an optical multiplier based on multiple reflection.

FIG. 1 shows schematically one embodiment for a photoacoustic detector of the present invention. As depicted in the figure, the photoacoustic detector comprises gas-filled chambers V and $V_0$, which contain or which can be supplied with a gas to be analyzed at a partial pressure $p_x$ and a carrier gas at a partial pressure $p_N$ (typically often nitrogen). The first chamber $V_0$ is composed of an annular housing element 1, having its first open end provided with a window 2 closing the first end of the chamber, through which infrared radiation or light in general can be guided into the chamber. The window 2 is preferably made highly transparent to infrared radiation and/or light and has preferably a thickness of about 3–6 mm. The chamber $V_0$ will be subsequently described in more detail regarding its dimensions and optimization thereof. The chamber $V_0$ has its second open end provided with a silicon door 3 closing the second end of the chamber at least partially, functioning as a pressure sensor, and having its design more closely depicted in FIGS. 8 and 9. The silicon door 3 can also be replaced with a microphone, a thin Mylar or metal film. Arranged as an extension to the second end of the first chamber $V_0$, the photoacoustic detector comprises a second chamber V, constituting a measuring space with a volume V. The measuring space is provided with measuring instruments for the silicon door movement. As shown in FIG. 1, the measuring space has its second end closed with a reference system, comprising a reference chamber $V_0$ which is closed at one end and identical to the first chamber $V_0$ in size. The reference chamber $V_0$ has its first end closed with a silicon door similar to that used for the first chamber.

The accuracy of a photoacoustic sensor can be improved by replacing the prior art measuring of a door or diaphragm movement with an optical measuring system of the present invention. Optical measuring causes very little interference with the movement of a door or a diaphragm. According to the present invention, the movement can be measured either by means of an angle assumed by a door or a diaphragm or by means of a translatory movement of some point in a door or a diaphragm.

FIG. 2 illustrates a measuring system based on angular measurement, which is provided with an optical indicator in the form of a laser 10, while its detector comprises a double detector 11. Besides a door 3, which serves as a sensor, the measuring system comprises the laser 10 as a light source, an optical lens 12 for focusing a light beam, and the double detector 11 for receiving and measuring a light beam v reflected from the door 3. Hence, the double detector comprises a first detector d1 and a second detector d2. The light beam has its focus 13 at the double detector. FIG. 3 depicts a light power of the measuring system on a double detector, wherein at each point of y the intensity of light is integrated in a direction perpendicular to y.

In the angular measurement shown in FIG. 2, an angle variation $\Delta\alpha$ is converted to a translatory motion $\Delta y = a2\Delta\alpha$, which is measured with a double detector $d_1 d_2$. The angle $\Delta\alpha$ represents an average angle variation in the door area illuminated by a laser beam. Generally, $\Delta\alpha$ depends on a measuring spot, i.e. l.

$$\tan\Delta\alpha = \frac{FL^2}{6EI}\left[1 - \left(\frac{L-l}{L}\right)^3\right] \quad (27)$$

$$= \frac{8EI\Delta x L^2}{6L^3 EI}\left[1 - \left(\frac{L-l}{L}\right)^3\right]$$

$$= \frac{4\Delta x}{3L}\left[1 - \left(\frac{L-l}{L}\right)^3\right],$$

or $$\Delta y \approx 2a\frac{4\Delta x}{3L}\left[1 - \left(\frac{L-l}{L}\right)^3\right]. \quad (28)$$

The smallest movement that can be measured with a double detector is $$\Delta y_{min} = \frac{\sigma}{2(S/N)}, \quad (29)$$

where $\sigma$ is the half width of a laser focus. At its minimum, $\sigma$ is limited by diffraction, i.e.

$$\sigma \approx \frac{\lambda}{D}(a+b). \quad (30)$$

Thus, the detectable minimum movement at the end of a door is $$\Delta x_{min} \approx \frac{3L\Delta y_{min}}{8a\left[1-\left(\frac{L-l}{L}\right)^3\right]} \quad (31)$$

$$= \frac{3L\lambda(a+b)}{2D(S/N)8a\left[1-\left(\frac{L-l}{L}\right)^3\right]}$$

$$= \frac{3L\lambda(a+b)}{16aD\left[1-\left(\frac{L-l}{L}\right)^3\right](S/N)}.$$

The illuminated area at the door has a width $aD/[(a+b)\cos\beta]$, which provides a final limitation. If $b \approx 0$ and $l \approx L$, the preceding equation results in $$\Delta x_{min} = \frac{3L\lambda}{16D(S/N)}. \quad (32)$$

In practice $D \leq L$, i.e.

$$\Delta x_{min} = \frac{3\lambda}{16(S/N)}, \quad (33)$$

where S is a laser intensity $I_0$ and N is a sum noise of light and electronics.

The amplitude of a signal (fluctuation of light power)

$$A_v = \Delta P_{d_1} - \Delta P_{d_2} = 2\Delta y I_{max}, \quad (34)$$

where $\Delta P_{d1}$ and $\Delta P_{d2}$ represent changes of light power at detectors $d_1$ and $d_2$, as well as $I_{max}$ is a maximum light power/$\Delta y$. Now, with the help of equation (28)

$$A_v = a\frac{16A_x I_{max}}{3L}\left[1-\left(\frac{L-l}{L}\right)^3\right] \approx \frac{16aA_x}{3L}\frac{P_{d_1}+P_{d_2}}{\sigma}\left[1-\left(\frac{L-l}{L}\right)^3\right], \quad (35)$$

where $P_{d1}+P_{d2}=I_0$ represent the light power of a laser falling on the double detector.

Thus, the optical indicator has a light signal whose amplitude is $$A_v = \frac{16aDI_0 A_x}{3L\lambda(a+b)} \approx \frac{16I_0 A_x}{3\lambda}, \quad (36)$$

where $A_x$ is the amplitude of door movement x, which must be $<\lambda$.

One of the benefits offered by an optical indicator of the present invention is its simple design, it does not interfere with door movement, and the double detector suppresses the photon noise of laser light. Preferably, the size of a laser light spot on the door is large, $D \approx L$, in order to have a small $\sigma$. The optical indicator of the present invention can also be used for measuring a diaphragm movement, the optimal measuring site being $r/\sqrt{3}$.

Thus, according to the present invention, the door movement can also be measured in a translatory measurement. FIG. 4 depicts a measuring system of the present invention, which is not an angular measurement and by which a translatory movement x of the door can be measured. In addition to the door, the measuring system comprises a laser 10 serving as a light source, a double detector 11, a first optical 12 lens for directing a light beam focus 13 to the surface of a door 3 presently at rest or in stationary condition, and a second optical lens 12 for focusing on the double detector a light beam reflected from the door 3. The light source, the optical lenses and the double detector are configured in such a way that, when the door is at rest, the angle between light beams incident on and reflecting from the door is 90 degrees. An advantage of the measurement is among other things that the laser beam is in focus at the door surface and the door may have a poor optical quality. The minimum movement that can be detected by the measuring system is $$\Delta_{min} \approx \frac{\sqrt{2}\, a\lambda}{4D(S/N)}, \quad (37)$$

if the door has a mirror surface.

The minimum movement is in the same order of magnitude as in angular measurement, i.e. $\Delta x_{min}=\lambda/(S/N)$, if $D=\sqrt{2}a/4$. Translatory measurement is also suitable for measuring a diaphragm movement, as well.

According to one preferred embodiment of the invention, the movement of a door or a diaphragm can also be measured optically by using an interferometer. FIG. 5 illustrates one measuring system of the present invention for measuring the movement of a door or a diaphragm by means of a so-called Michelson interferometer. As shown in the figure, the system comprises, in addition to the door itself, a laser 10 serving as a light source, an optical lens 12 for focusing a laser beam, a beam splitter 15 or a semi-transparent mirror for splitting the laser beam for the door and for a reference mirror 16, the reference mirror 16 and a triple detector 17 for receiving the laser beams coming from the beam splitter 15. According to what is shown in the figure, the laser beam is approximately in focus both at the door and at the reference mirror. The reference mirror 16 is adjusted such that the triple detector 17, constituted by three sensors d1, d2 and d3, develops ¾ of the interference fringe perpendicular to the plane of paper. When x changes as the door is moving, the interference fringe moves laterally across the detectors, as shown in FIG. 6. The fringe moves across a single fringe gap, when x changes by $\lambda/2$. The intensity distribution of the fringe is $$I(z) = \frac{1}{2}A\left[1+\cos\left(2\pi\frac{z}{D}\right)\right]. \quad (38)$$

If the interference fringe moves by $\epsilon$, signals $I_1$, $I_2$ and $I_3$ of the sensors $d_1$, $d_2$ and $d_3$ are obtained as follows:

$$I_1(\varepsilon) = \int_{\frac{2D}{4}+\varepsilon}^{-\frac{D}{4}+\varepsilon} \frac{A}{2}\left[1 + \cos\left(2\pi\frac{z}{D}\right)\right]dz \qquad (39)$$

$$= \frac{AD}{2\cdot 4} + \frac{AD}{2\cdot 2\pi}\left[-\cos\left(2\pi\frac{\varepsilon}{D}\right) + \sin\left(2\pi\frac{\varepsilon}{D}\right)\right],$$

$$I_2(\varepsilon) = \int_{\frac{D}{4}+\varepsilon}^{\varepsilon} \frac{A}{2}\left[1 + \cos\left(2\pi\frac{z}{D}\right)\right]dz \qquad (40)$$

$$= \frac{AD}{2\cdot 4} + \frac{AD}{2\cdot 2\pi}\left[\cos\left(2\pi\frac{\varepsilon}{D}\right) + \sin\left(2\pi\frac{\varepsilon}{D}\right)\right] \text{ and}$$

$$I_3(\varepsilon) = \int_{\varepsilon}^{\frac{D}{4}+\varepsilon} \frac{A}{2}\left[1 + \cos\left(2\pi\frac{z}{D}\right)\right]dz \qquad (41)$$

$$= \frac{AD}{2\cdot 4} + \frac{AD}{2\cdot 2\pi}\left[\cos\left(2\pi\frac{\varepsilon}{D}\right) - \sin\left(2\pi\frac{\varepsilon}{D}\right)\right].$$

Thus, (42)

$$\begin{cases} I_2(\varepsilon) - I_1(\varepsilon) = \frac{AD}{2\pi}\cos\left(2\pi\frac{\varepsilon}{D}\right) \\ I_2(\varepsilon) - I_3(\varepsilon) = \frac{AD}{2\pi}\sin\left(2\pi\frac{\varepsilon}{D}\right) \end{cases}$$

or $$\frac{2\pi\varepsilon}{D} = \tan^{-1}\left\{\frac{I_2 - I_3}{I_2 - I_1}\right\}. \qquad (43)$$

Because $\varepsilon = \Delta z = 2D\Delta x/\lambda$, then $$\Delta x = \frac{\lambda}{4\pi}\tan^{-1}\left\{\frac{I_2 - I_3}{I_2 - I_1}\right\} \qquad (44)$$

Since the signals $I_1$, $I_2$ and $I_3$ are in a 90° phase relative to each other and hence also the signals $I_2-I_1$ and $I_2-I_3$ are in a 90° phase relative to each other, they can provide a way across tangent function discontinuities shown in FIG. 7. Hence, in equation $$\Delta x = \left(k + \frac{1}{2}\right)\frac{\lambda}{4} + \frac{\lambda}{4\pi}\tan^{-1}\left\{\frac{I_2 - I_3}{I_2 - I_1}\right\}$$

it is possible to measure changes ±1 of an integer k at tangent discontinuities $\phi=(n+\frac{1}{2})\pi$.

The smallest detectable movement is $$\Delta x_{min} = \frac{\sigma}{2(S/N)} = \frac{\lambda}{8(S/N)}, \qquad (45)$$

where $S=I_0/2$.

If the door movement is small $<\lambda/4$, the triple detector of the above-described measuring system can be replaced by a double detector the same way as in the optical indicator. Thus, the combined width of the sensors is equal to the width of a single fringe and $$\begin{cases} I_1 + I_2 = \frac{AD}{2} = \frac{I_0}{2} \\ I_1 - I_2 = \frac{AD}{\pi}\sin\left(2\pi\frac{\varepsilon}{D}\right) \end{cases} \qquad (46)$$

Because $\varepsilon = \Delta z = 2D\Delta x/\lambda$ is $$\Delta x = \frac{\lambda}{4\pi}\sin^{-1}\left\{\frac{I_1 - I_2}{I_1 + I_2}\right\} \approx \frac{\lambda}{8}\frac{I_1 - I_2}{I_1 + I_2} = \frac{\lambda}{4I_0}(I_1 - I_2), \qquad (47)$$

where $I_0$ is the laser light power. Then, the amplitude of the light signal is $$A_l = I_1 - I_2 \approx 4\frac{I_0 A_x}{\lambda}, \qquad (48)$$

where $A_x$ is the amplitude of the door movement x.

Thus, the basic idea in a measuring system based on the use of an interferometric triple detector is the necessity of providing three signals with a 90° phase difference relative to each other. Hence, the use of these three signals enables the elimination of an error factor, a dc-component, resulting from the possible flashing of a light source. Consequently, the interferometric measurement can also be effected by such adjustment of the interferometer that the space between fringes on the detectors is basically infinite, whereby the measurement is not performed on the basis of a movement of the fringes. In addition to this, the interferometer is adjusted in such a way that the light source is set relative to the beam splitter at an angle other than a 45-degree angle, whereby the light beam reflecting from both a door (or a diaphragm) and from a reference mirror, the focus of which is at the door (or the diaphragm) and at the reference mirror, does not return along precisely the same path, but, instead, there is a small angle between the outbound light beam and inbound light beam. In this case, the triple detector for measuring returning light beams can be designed in such a way that two detectors, which constitute a double detector, are adapted to measure the light beam returning from a door (or a diaphragm) and reflected from a beam splitter, as well as the light beam returning from a reference mirror and passing through the beam splitter. The third detector is adapted to measure the light beam returning from a door (or a diaphragm) and passing through a beam splitter, as well as the light beam reflected from a reference mirror and the beam splitter (the third detector is preferably placed in the proximity of a light source). In addition, when the traveling path of a light beam returning from a reference mirror is provided with two elements, such as two glass panels, of which at least one having its position adjustable, it is possible, by adjusting the position of said elements, to provide a 90° phase difference between the measuring signals of detectors establishing a double detector. This results in three signals $I_1$, $I_2$ and $I_3$, which are in a 90° phase difference relative to each other.

Advantages gained by interferometric measurement according to the present invention include e.g.: According to equation (44), the response is highly linear even when the movement of a door or a diaphragm covers several wavelengths. Absolute accuracy is high, because the shape of an interference signal is precisely consistent with ½(1+cos (2πz/D)). In addition, a laser can be focused on the measuring point of a door in an almost dot-like manner and the result is not affected by diffraction. Neither is the value of a measuring result affected by fluctuation of the laser intensity $I_0$, since the value of the maximum intensity A is reduced away in equation (44).

As stated above, for the detection of pressure fluctuations occurring in a first chamber, the measuring system of the present invention may employ both a per se known diaphragm that can be stressed or unstressed or, according to a highly preferred embodiment of the present invention, for example a silicon-made door, the use of which upgrades the measuring accuracy and sensitivity of a photoacoustic detector even further. In addition, hereinbelow will be described a method for the optimization of a door or a diaphragm.

FIGS. 8 and 9 depict schematically and by way of example one preferred silicon-made door, functioning as a pressure sensor and applicable in a photoacoustic detector of the present invention. The pressure sensor comprises a panel-like skirt member serving as a door frame, and a door separated by a slit from the panel-like member. L is a width of the door, h its height, d its thickness, and $\Delta$ a width of the slot.

With low IR outputs of a light source conductible through the window into the chamber in a state of equilibrium, when $W(t)=W_{av}+W_0 \cos(2\pi ft)$, there follows $$\left(\frac{dT}{dt}\right) = \frac{a_x p_x 2l(\cos\alpha)^{-1} W_0 \cos(2\pi ft)}{\sum_i c_V^i m_i} \quad (1)$$

$$= \frac{a_x p_x 2l(\cos\alpha)^{-1} W_0 \cos(2\pi ft)}{V_0 \sum_i c_V^i \rho_i},$$

where $a_x$ is an absorption coefficient for a gas at a partial pressure $p_x$, $l$ is a length of the chamber, $\alpha$ is an angle between the IR beam and the centre axis of the chamber, and $W(t)$ is a net light power proceeding into the chamber. That is, $W(t)$ is the light intensity$\times \pi R^2$, wherein R is a radius of the chamber, $m_i$ is a mass of the gas component, $c_V^i$ is a specific heat capacity of the corresponding gas, $\rho_i$ is a density of the gas i, and $V_0$ is a volume of the smaller chamber. For example $$\sum_i c_V^i m_i = c_V^x m_x + c_V^N m_N = V_0(c_V^x \rho_x + c_V^N \rho_N).$$

It is a default in equation (1) that $\tau \ll f^{-1} \ll \tau_0$, wherein $\tau_0$ is a time constant for heat conduction out of the chamber and $\tau$ is a time constant for the conversion of absorption energy to heat.

Further $$\Delta T = T(t) - T_0 = \int \left(\frac{dT}{dt}\right)_{T_0} dt = \frac{a_x p_x 2l(\cos\alpha)^{-1} W_0 \sin(2\pi ft)}{2\pi f V_0 \sum_i c_V^i \rho_i}. \quad (2)$$

An equation of state for the ideal gas results in $$\frac{dp}{p_0} + \frac{dV}{V_0} = \frac{dT}{T_0}. \quad (3)$$

In the pressure sensor:

$$dV \approx \frac{1}{2} xA \quad (4)$$

$$A dp = kx = F,$$

where A represents a surface area of the pressure sensor, k is a spring constant, and x is a motion. From equations (3) and (4) is obtained $$x \approx \frac{\Delta T/T_0}{\frac{k}{Ap_0} + \frac{A}{2V_0}} \quad (\omega = 0). \quad (5)$$

Because $\Delta T$ presented in equation (2) is modulated by an angular frequency $\omega$, it is necessary to examine an equation of motion for the door (or the diaphragm), i.e.

$$m\ddot{x} - 2\beta m\dot{x} \underbrace{m\omega_0^2 x}_{k} = F_0 e^{i\omega t}, \quad (6)$$

where $F_0 e^{i\omega t}$ represents a periodic force, $\beta$ is an damping constant, $\omega_0 = \sqrt{k/m}$ is a resonance angular frequency, and x is a motion either from the end of a door or from the middle of a door or a diaphragm. The solution for equation (6)

$$x = \frac{(F_0/m)e^{i\omega t}}{\omega_0^2 - \omega^2 + 2i\omega\beta}, \quad (7)$$

from which is obtained an amplitude $$\sqrt{x * x} = A_x(\omega) = \frac{F_0/m}{\sqrt{(\omega_0^2 - \omega^2)^2 + 4\beta^2 \omega^2}}. \quad (8)$$

Equations (3) and (4) provide for amplitudes $$\frac{\Delta p}{p_0} = \frac{\Delta T}{T_0} - \frac{\Delta V}{V_0} = \frac{\Delta T}{T_0} - \frac{1}{2} A_x(\omega) \frac{A}{V_0} \quad (9)$$

and hence $$A_x(\omega) = \frac{A\Delta p/m}{\sqrt{(\omega_0^2 - \omega^2)^2 + 4\beta^2 \omega^2}}$$

$$= \frac{Ap_0 \left(\frac{\Delta T}{T_0} - \frac{A_x(\omega)A}{2V_0}\right)}{m\sqrt{(\omega_0^2 - \omega^2)^2 + 4\beta^2 \omega^2}},$$

from which $$A_x(\omega) = \frac{Ap_0 \frac{\Delta T}{T_0}}{m\sqrt{(\omega_0^2 - \omega^2)^2 + 4\beta^2 \omega^2} + \frac{p_0 A^2}{2V_0}}.$$

FIG. 10*a* shows schematically the effect of a resonance angular frequency $\omega_0$ on a door or diaphragm amplitude $A_x(\omega)$.

If $\omega=0$, then equation (9) results in equation (5), i.e. $A_x(0)=x$, because $m\omega_0^2=k$.

It is preferred that the resonance of a door or a diaphragm be modelled in such a way that the increase of amplitude brought by resonance around $\omega_0$ is not taken into consideration (see FIG. 10*b*). That is, if $\omega < \omega_0$, the result is $$A_x(\omega) \approx \frac{Ap_0 \Delta T/T_0}{m\omega_0^2 + \frac{p_0 A^2}{2V_0}} = \frac{p_0 \Delta T/T_0}{\frac{m\omega_0^2}{A} + \frac{p_0 A}{2V_0}} = \frac{p_0 \Delta T/T_0}{\rho d\omega_0^2 + \frac{p_0 A}{2V_0}}, \quad (10)$$

and if $\omega > \omega_0$, the result is $$A_x(\omega) = \frac{p_0 \Delta T/T_0}{\rho d\omega^2 + \frac{p_0 A}{2V_0}}, \quad (11)$$

where $\rho$ represents a door or diaphragm density and d is a thickness. If resonance is not utilized, it is advisable to use a door or a diaphragm at less than the resonance angle frequency $\omega_0$, i.e. to use equation (10), which indicates that the optimization, i.e. maximization, of amplitude $A_x(\omega)$ must be done by means of $\omega_0$, d, $V_0$ and A. The lower $\omega_0$ and A are, the higher is $A_x(\omega)$.

Amplitude reaches a maximum, when $\rho d\omega_0^2 + P_0^A/2V_0$ reaches a minimum. This happens when $$\rho d\omega_0^2 \approx \frac{p_0 A}{2V_0} \quad (12)$$

and $$A_x^{opt}(\omega) = \frac{p_0 \Delta T/T_0}{2\rho d\omega_0^2} = \frac{p_0 \Delta T/T_0}{2 \frac{p_0 A}{2V_0}} \quad (13)$$

By means of equations (1) and (2), the result from equation (13) is $$A_x^{opt}(\omega) = \frac{p_0 a_x p_x l(\cos\alpha)^{-1} W_0}{T_0 \omega V_0 \sum_i c_V^i \rho_i \rho d\omega_0^2}, \quad (14)$$

where $\omega \leq \omega_0$. The equation indicates that the best way to augment a response is to reduce angular frequencies $\omega$ and $\omega_0$. With typical commercially available microphones, the resonance frequency $f_0 = \omega_0/2\pi$ is typically 10–20 kHz. If a microphone, whose resonance frequency $f_0 = 20$ kHz, is operated close to the resonance frequency, the result is $A_x^{opt}$ (20 kHz). If a similar diaphragm is used to construct a new microphone, whose resonance frequency $f_0 = 500$ Hz, then $$A_x^{opt}(500 \text{ Hz}) = \left(\frac{20 \text{ kHz}}{0.5 \text{ kHz}}\right)^3 A_x^{opt}(20 \text{ kHz}) = \quad (15)$$
$$40^3 A_x^{opt}(20 \text{ kHz}) = 64000 A_x^{opt}(20 \text{ kHz}),$$

provided that the microphones are optimized according to equation (12). Further, if a microphone optimized for the frequency of 500 Hz were operated at the frequency of 50 Hz, the response would further grow tenfold and the improvement factor would thus be 640000. The resonance frequency can be decreased on the basis of a subsequent equation (16) by making a door or a diaphragm thinner. This provides a further improvement at a ratio $d_1/d_2$ provided that the thinning of a door or a diaphragm is technically possible.

Resonance angular frequencies depend on the dimensions and material of a door or a diaphragm. For a door $$\omega_0 = \sqrt{\frac{2E}{3\rho}} \frac{d}{L^2}, A = Lh, \quad (16)$$

where E is a Young's modulus for the material, $\rho$ is a density, L is a width of the door, h is a height, and d is a thickness.

For a circular metal diaphragm, which is not under tension $$_E\omega_0 = \sqrt{\frac{E}{3\rho(1-\sigma^2)}} \frac{4d}{r^2}, \quad (17)$$

where $\sigma$ = Poisson's ratio and r is a radius of the diaphragm.

For a tensioned thin film (for example Mylar)

$$_T\omega_0 = \frac{2.4\sqrt{T/\mu}}{r} = \frac{2.4}{r}\sqrt{\frac{F}{2\pi r \rho d}}, \quad (18)$$

where T represents a tension of the film and $\mu$ is a mass/unit area, i.e. $\mu = m/a = \rho dA/A = \rho d$.

To be exact, even for a tin film (Mylar 2 μm) applies $$\omega_{tod}^2 = {_E\omega_0^2} + {_T\omega_0^2}, \quad (19)$$

where nevertheless $_E\omega_0^2 \ll {_T\omega_0^2}$.

If comparison is made between a door according to one exemplary embodiment of the present invention, fabricated from the same material (silicon) and having a height L/s, with a circular diaphragm not under tension, the result will be $$\frac{A_{door}^{opt}}{A_{film}^{opt}} \approx s\pi \left[\frac{8}{s\pi(1-\sigma^2)}\right]^{1/3} \approx 20, \quad (20)$$

if s=10, i.e. the door has a height which is one tenth of the width L.

If comparison is made between a door according to one exemplary embodiment of the present invention with a tensioned Mylar film usually employed in prior art microphones, the result will be $$\frac{A_{door}^{opt}}{A_{Mylar}^{opt}} \approx 43\left(\frac{F}{N}\right)^{2/5}, \quad (21)$$

where F represents a total tensile force in Newtons and s=10. The ratio is typically 10–20, depending on how little force F is required to make the film functional.

Thus, a door according to the present invention provides a solution which imparts an improvement of at least one order of magnitude in the response of a sensor. If this improvement is added to that gained by angular frequency, a low resonance door can be created which provides in a highly advantageous manner an improvement of a few million in the response of a sensor.

The use of a door-sensor according to one embodiment of the present invention requires that a slot or gap between the door and the wall be preferably made as narrow as possible. The chamber leaks through the gap, with the result that the sensor has a lower limiting frequency $f_{cut}$, which is defined by a door gap area a as follows:

$$f_{cut} \propto v_0 \frac{a}{V_0}, \quad (22)$$

where $v_0$ is a velocity of sound in the chamber and $V \gg V_0$.

On the other hand, it is beneficial to have a small hole between the chambers for equalizing slow pressure variations between the chambers, and which hole can thus be designed as the above-mentioned gap between the door and the door frame.

When comparing the optical indicator and the interferometer with each other, it can be concluded that the equation (33) does not work out in practice, because a square (rectangular) door is not the optimal form when optimizing the equation (10). That is, in other words, the optical indicator and the interferometer of the present invention function very well also with a square (rectangular) door, but should a further improvement in sensitivity and accuracy be desired, the door shape must be changed. When using a door whose height is one tenth of its width L (i.e. s=10), according to FIG. 11 the equation (31) results in $$\Delta x_{min} \approx \frac{3L\lambda}{16L/10(S/N)} \approx \frac{2\lambda}{S/N}, \quad (49)$$

which is 16-fold with respect to the corresponding value of an interferometer (equation (45)). Further, the interferometer will be improved with respect to the optical indicator, if s grows, i.e. the door becomes shorter, which, on the other hand, also increases the amplitude $A_x(\omega)$ of door movement.

The configuration of a door can still be improved, for example by further reducing a resonance frequency by weakening a door hinge by grooving the hinge in its midsection as shown in FIG. 12a and/or by augmenting the surface area of a door at the end of the door as shown in FIG. 12b. The door design shown in FIG. 12b is particularly suitable for the multiplier solution of an interferometer as described in more detail hereinafter.

Since the use of an interferometer develops an almost dot-like spot on the door, it is possible to apply multiple reflection, i.e. a multiplier, in the interferometer as shown in FIG. 13. Laser light travels to an end mirror 21, reflecting n times from the door and from a fixed plane mirror 20, which is mounted in the vicinity of the door and preferably set parallel to the door surface. The laser has its focus in the proximity of the end mirror, from which the laser beam returns along the same path, reflecting another n times from the door. If the door nudges a distance $\Delta x$, the optical distance changes in the interferometer by $4n\Delta x$ and the response increases 2n fold, if there are no reflection losses.

If the mirrors and the door have a reflection coefficient R, the equation (45) adopts now a new form:

$$R x_{min} = \frac{\lambda}{2nR^{4n-2}8(S/N)} = \frac{x_{min}}{2nR^{4n-2}}. \quad (50)$$

This method provides about a 10-fold augmentation of sensitivity. Multiple reflection can also be applied in a laser reflection of the present invention for translatory measurement, since the laser has its focus on the door.

When comparing an optical indicator of the present invention and an interferometer with each other, it can be concluded that both measuring systems of the present invention are capable of providing a substantial improvement regarding the accuracy and sensitivity of measurement. Interferometric measurement is even somewhat more precise than an optical indicator, but at the same time the measuring system is slightly more complicated. Hence, the required sensitivity should be considered in light of a specific application and case for selecting the appropriate measuring method.

As stated above, a problem with prior known photodetectors is disturbance caused by external sounds. According to the present invention, the effect of external sounds can be suppressed by means of a per se known double detector, which is shown in FIG. 1. According to the present invention, the actual measuring signal and a reference signal are measured separately and calculated for their amplitudes, the difference therebetween enabling a more accurate and effective filtration of external noises. Especially in a frequency range, where there is no signal developed by a gas, the interfering noise can be substantially reduced. The above type of interference elimination method is applicable not only to a photoacoustic detector as described above but to others as well. Therefore, the interference elimination method of the present invention is also capable of upgrading the operation of photoacoustic detectors based on the use of traditional microphones, for example.

There is no intention whatsoever to limit the invention to the embodiment described in the foregoing disclosure, but it can be varied within the scope of the inventive concept set forth in the claims. Thus, for example, the double and triple detectors used in the foregoing examples can be replaced by a CCD array detector or some other multidetector comprising several detectors, because the number of detectors or separate measuring signals presented in the examples only represents the number of measuring signals which is at least required.

LITERATURE REFERENCES

[1] Nicolas Ledermann et. al., Integrated Ferroelectrics, Vol. 35, pp. 177–184 (2001)
[2] M. H. de Paula et. al., J. Appl. Phys., Vol. 64, 3722–3724 (1988)
[3] M. H. de Paula et al., Rev. Sci. Instrum., Vol. 673, 3487–3491 (1992)

The invention claimed is:
1. A photoacoustic detector, comprising at least
   a first chamber suppliable with a gas to be analyzed,
   a window for letting modulated and/or pulsed infrared radiation and/or light in the first chamber,
   a second chamber, which constitutes a measuring space with a volume V and which is in communication with the first chamber by way of an aperture provided in a wall of the first chamber,
   at least one sensor, which is arranged in the wall aperture of the first chamber and adapted to be movable in response to pressure variations produced in the first chamber by absorbed infrared radiation and/or light, and
   means for measuring the sensor movement optically by using an interferometer comprising at least a light source, a reference mirror, a beam splitter or a semitransparent mirror for splitting the beam for the sensor and for the reference mirror of the interferometer, and at least three detectors for receiving light beams coming from the beam splitter, wherein the interferometer is arranged to provide at least three measuring signals in different phase relative to each other.

2. A photoacoustic detector as set forth in claim 1, wherein the phase difference between at least three measuring signals from the detectors receiving the light beams is 90°.

3. A photoacoustic detector as set forth in claim 1, wherein the interferometer comprises additionally at least an optical lens for focusing a beam from the light source approximately on a sensor surface.

4. A photoacoustic detector as set forth in claim 3, wherein the focus of a light beam emitted by light source is arranged approximately on a sensor surface and at the reference mirror.

5. A photoacoustic detector as set forth in claim 1, wherein the detectors receiving the light beams from the beam splitter are arranged to form a row detector.

6. A photoacoustic detector as set forth in claim 1, wherein the reference mirror is adjusted to provide phase difference between the measuring signals.

7. A photoacoustic detector as set forth in claim 1, wherein traveling path of a light beam returning from the reference mirror is provided with two elements, such as two glass panels, of which at least one having its position adjustable to provide phase difference between the measuring signals.

8. A photoacoustic detector as set forth in claim 1, wherein the detectors for measuring returning light beams can be designed in such a way that some of the detectors, for example two detectors, are adapted to measure the light beam returning from the sensor and reflected from the beam splitter, as well as the light beam returning from the reference mirror and passing through the beam splitter and some of the detectors, for example a third detector, is adapted to measure the light beam returning from the sensor and passing through the beam splitter, as well as the light beam reflected from the reference mirror and the beam splitter.

9. A photoacoustic detector as set forth in claim 1, wherein the light source is a laser.

10. A photoacoustic detector as set forth in claim 1, further comprising a third chamber, which is closed and identical to the first chamber in terms of size and has an aperture which is identical to that included in the first chamber and connects the third chamber with the second chamber, and said aperture of the third chamber being closed with a sensor similar to that closing the aperture of the first chamber, and the movement of said sensor being measured in a manner similar to that used for measuring the movement of a sensor closing the first chamber aperture, as well as means for calculating the amplitudes of an actual measuring signal measured from the sensor fitted in the first chamber aperture and a reference signal measured from the sensor fitted in the third chamber aperture, and for working out a difference therebetween.

11. A measuring system in a photoacoustic detector for measuring the movement of a sensor in a photoacoustic detector, the system comprising at least a light source, a reference mirror, a beam splitter or a semi-transparent mirror for splitting the beam for the sensor and for the reference mirror of the interferometer, and at least three detectors for receiving light beams coming from the beam splitter, wherein the interferometer is arranged to provide at least three measuring signals in different phase relative to each other.

12. A measuring system as set forth in claim 11, wherein the phase difference between at least three measuring signals from the detectors receiving the light beams is 90°.

13. A measuring system as set forth in claim 11, wherein the measuring system comprises additionally at least an optical lens for focusing a beam from the light source approximately on a sensor surface.

14. A measuring system as set forth in claim 13, wherein the focus of a light beam emitted by light source is arranged approximately on a sensor surface and at the reference mirror.

15. A measuring system as set forth in claim 12, wherein the detectors receiving the light beams from the beam splitter are arranged to form a row detector.

16. A measuring system as set forth in claim 12, wherein the reference mirror is adjusted to provide phase difference between the measuring signals.

17. A measuring system as set forth in claim 12, wherein traveling path of a light beam returning from the reference mirror is provided with two elements, such as two glass panels, of which at least one having its position adjustable to provide phase difference between the measuring signals.

18. A measuring system as set forth in claim 12, wherein the detectors for measuring returning light beams can be designed in such a way that some of the detectors, for example two detectors, are adapted to measure the light beam returning from the sensor and reflected from the beam splitter, as well as the light beam returning from the reference mirror and passing through the beam splitter and some of the detectors, for example a third detector, is adapted to measure the light beam returning from the sensor and passing through the beam splitter, as well as the light beam reflected from the reference mirror and the beam splitter.

19. A measuring system as set forth in claim 12, wherein the light source is a laser.

20. A method for measuring the movement of a sensor in a photoacoustic detector, wherein the measurement is implemented as an optical measurement, the sensor or a part thereof being illuminated and light reflected from the sensor being measured by means of a multi-detector detector, and the sensor movement is measured as translatory measurement by using an interferometer comprising at least a light source, a reference mirror, a beam splitter or a semi-transparent mirror for splitting the beam for the sensor and for the reference mirror of the interferometer, and at least three detectors for receiving light beams coming from the beam splitter, wherein the interferometer is arranged to provide at least three measuring signals in different phase relative to each other.

* * * * *